(12) United States Patent
Wantink

(10) Patent No.: US 6,692,461 B2
(45) Date of Patent: Feb. 17, 2004

(54) CATHETER TIP

(75) Inventor: Kenneth L. Wantink, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/924,380

(22) Filed: Aug. 7, 2001

(65) Prior Publication Data

US 2003/0032920 A1 Feb. 13, 2003

(51) Int. Cl.[7] .............................................. A61M 29/00
(52) U.S. Cl. ..................................... 604/103; 604/96.01
(58) Field of Search .......................... 604/96.01, 103, 604/164.01, 164.03, 164.13, 523, 264

(56) References Cited

U.S. PATENT DOCUMENTS

| | | | |
|---|---|---|---|
| 3,832,253 A | 8/1974 | Di Palma et al. ............. 156/86 |
| 3,865,666 A | 2/1975 | Shoney ....................... 156/245 |
| 3,884,242 A | 5/1975 | Bazell et al. ................ 128/351 |
| 4,157,094 A | 6/1979 | Patel .......................... 128/349 |
| 4,276,874 A | 7/1981 | Wolvek et al. ................. 128/1 |
| 4,385,635 A | 5/1983 | Ruiz ........................... 128/658 |
| 4,413,989 A | 11/1983 | Schjeldahl et al. ........... 604/96 |
| 4,496,345 A | 1/1985 | Hassoon ...................... 604/103 |
| 4,540,404 A | 9/1985 | Wolvek ......................... 604/96 |
| 4,702,252 A | 10/1987 | Brooks et al. ............... 128/344 |
| 4,706,670 A | 11/1987 | Andersen et al. ............ 128/344 |
| 4,782,834 A | 11/1988 | Maguire et al. ............. 128/344 |
| 4,892,519 A | 1/1990 | Songer et al. |
| 4,917,667 A | 4/1990 | Jackson ........................ 604/96 |
| 4,921,483 A | 5/1990 | Wijay et al. ................... 604/96 |
| 5,078,702 A | 1/1992 | Pomeranz .................... 604/280 |
| 5,160,559 A | 11/1992 | Scovil et al. |
| 5,171,232 A | 12/1992 | Castillo et al. .............. 604/280 |
| 5,176,698 A * | 1/1993 | Burns et al. ................. 606/192 |
| 5,234,416 A | 8/1993 | Macaulay et al. ........... 604/282 |
| 5,250,069 A | 10/1993 | Nobuyoshi et al. .......... 606/192 |
| 5,267,959 A | 12/1993 | Forman ....................... 604/103 |
| 5,366,442 A | 11/1994 | Wang et al. ................. 604/103 |
| 5,378,236 A * | 1/1995 | Seifert ......................... 604/96 |
| 5,425,712 A | 6/1995 | Goodin ......................... 604/96 |
| 5,522,800 A * | 6/1996 | Crocker ........................ 604/96 |
| 5,697,906 A | 12/1997 | Ariola et al. .................. 604/96 |
| 5,728,063 A | 3/1998 | Preissman et al. ............ 604/96 |
| 5,728,065 A | 3/1998 | Follmer et al. ............... 604/96 |
| 5,762,637 A | 6/1998 | Berg et al. ................... 604/264 |
| 5,769,819 A | 6/1998 | Schwab et al. .............. 604/103 |
| 5,769,830 A | 6/1998 | Parker ......................... 604/282 |
| 5,792,124 A * | 8/1998 | Horrigan et al. ............. 604/282 |
| 5,827,225 A | 10/1998 | Ma Schwab .................. 604/96 |
| 5,843,090 A | 12/1998 | Schuetz ....................... 606/108 |
| 5,891,110 A | 4/1999 | Larson et al. ................ 604/280 |
| 6,325,790 B1 * | 12/2001 | Trotta .......................... 604/523 |
| 6,368,301 B1 * | 4/2002 | Hamilton et al. ............ 604/103 |

FOREIGN PATENT DOCUMENTS

| | | |
|---|---|---|
| DE | 3900635 A1 | 1/1989 |
| EP | 0517075 A1 | 5/1992 |
| EP | 0 597 465 A1 | 5/1994 |
| EP | 0 742 029 A1 | 11/1996 |
| GB | 2337094 A | 4/1999 |
| WO | WO 99/44666 | 2/1999 |
| WO | WO 01/45783 A2 | 6/2001 |

* cited by examiner

*Primary Examiner*—Long V. Le
*Assistant Examiner*—Ann Y. Lam
(74) *Attorney, Agent, or Firm*—Fulwider Patton Lee & Utecht, LLP

(57) ABSTRACT

A balloon catheter having an improved maneuverability. The catheter includes an elongated catheter shaft with proximal and distal ends, proximal and distal shaft sections, a balloon on the distal catheter shaft section having proximal and distal shaft sections, a guidewire receiving lumen extending along at least a portion of the catheter shaft to the catheter shaft distal end, and a tip member on a distal end of the catheter. A proximal end of the tip member is spaced distally apart from the distal end of the catheter shaft and is in fluid communication therewith. The distal balloon shaft is sealingly secured to the catheter shaft and the tip member.

8 Claims, 6 Drawing Sheets

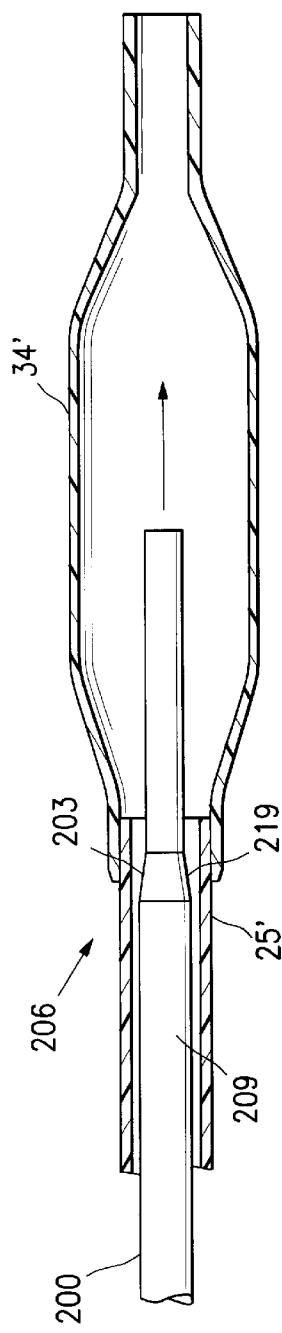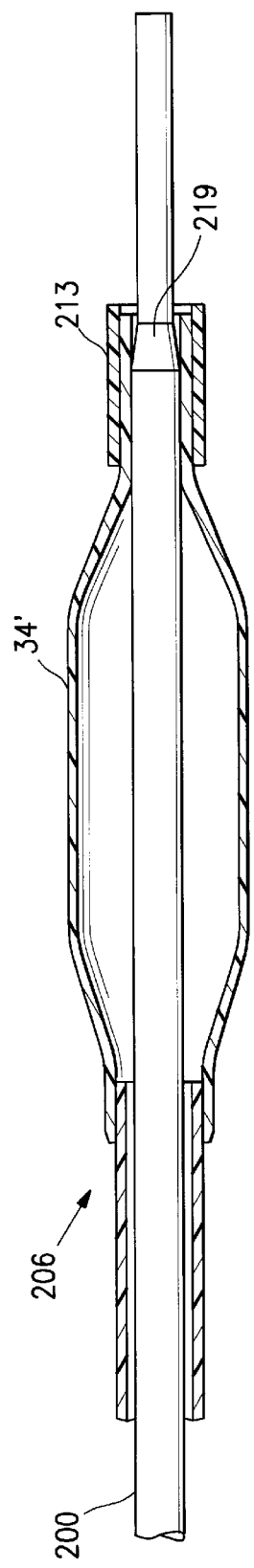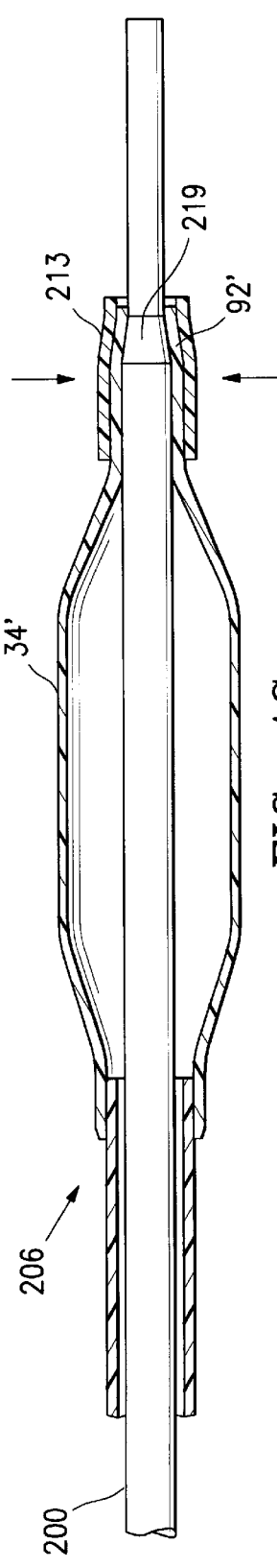

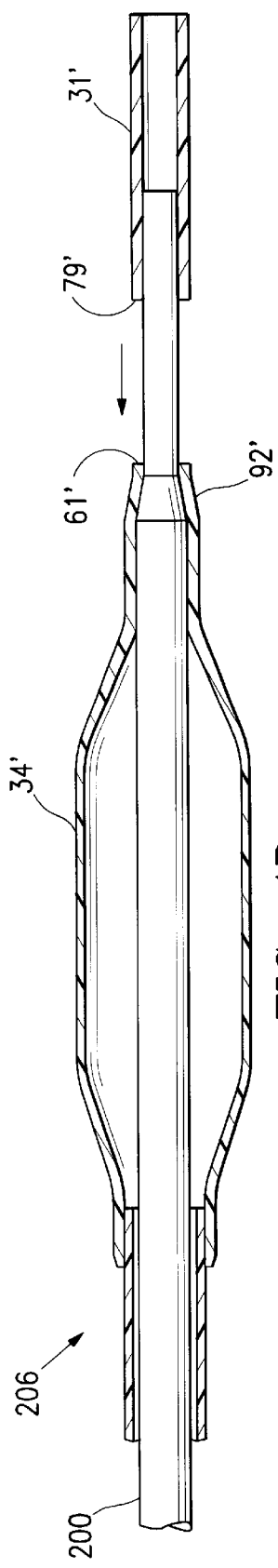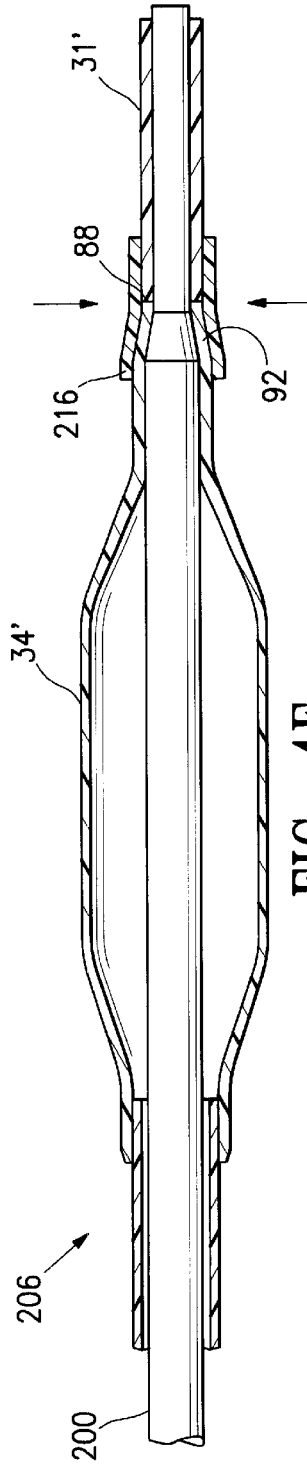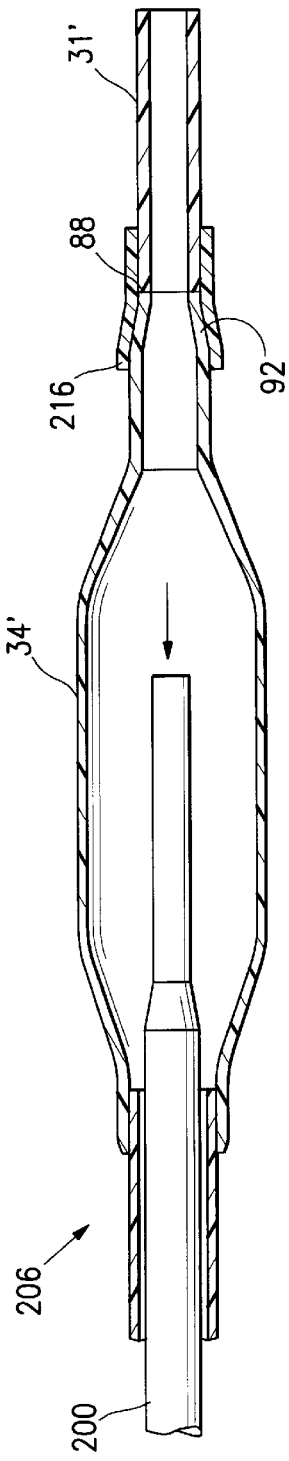

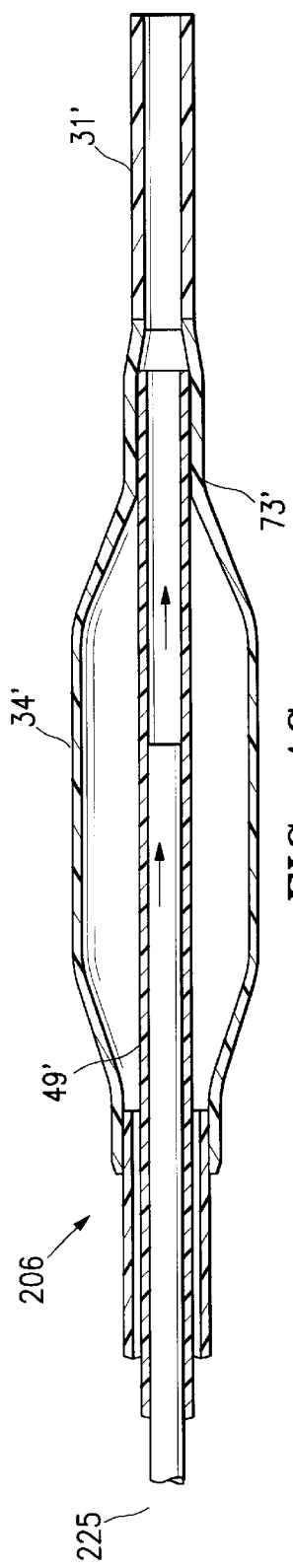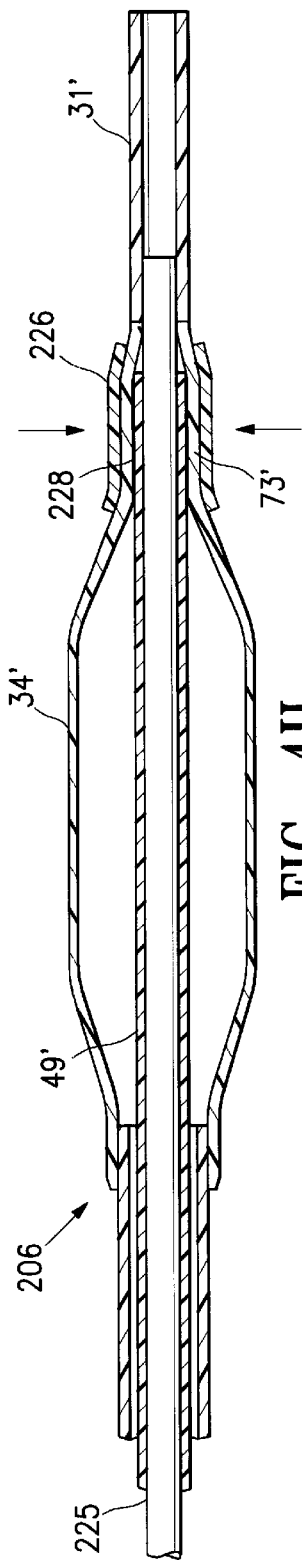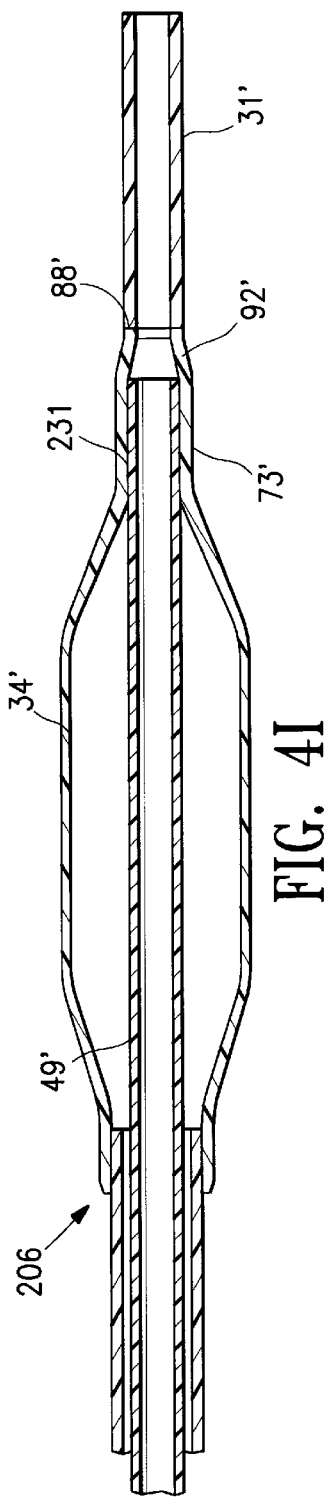

CATHETER TIP

FIELD OF INVENTION

This invention generally relates to medical devices, and particularly to intraluminal catheters.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion.

Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

Catheters designed for intravascular procedures such as angioplasty have a number of design considerations. Such catheters must be able to transmit force along the length of the catheter shaft so that the catheter can be pushed through the patient's vasculature. However, the catheter shaft must also have sufficient flexibility to allow the catheter to track over a guidewire through tortuous vasculature as well as crossing stenosed portions of the vascular anatomy.

Prior art intravascular catheters have commonly included a soft distal tip to prevent or minimize injury to the vessel during advancement of the catheter therein. One difficulty has been forming a connection between the soft tip and the catheter which is sufficiently strong to prevent disengagement of the soft tip or kinking at the junction between the soft tip and catheter shaft. Additionally, it is necessary to balance the strength of the connection between the soft tip and the catheter shaft with the need to minimize the stiffness of the distal end of the catheter. Minimizing the stiffness of the distal end of the catheter results in improved maneuverability of the catheter.

Accordingly, it would be a significant advance to provide a catheter with a soft tip having improved performance. This invention satisfies these and other needs.

SUMMARY OF THE INVENTION

The present invention is directed to balloon catheter with improved maneuverability. The catheter includes an elongated catheter shaft having a proximal end, a distal end, proximal and distal shaft sections. A guidewire receiving lumen extends along at least a portion of the catheter shaft to a port of the distal end of the catheter shaft. An inflation lumen extends along at least a portion of the catheter shaft terminating at a point proximal to the distal end of the catheter shaft.

The catheter further includes a tip member on the distal end of the catheter with a proximal end of the tip member spaced distally apart from the distal end of the catheter shaft. A lumen of the tip member is in fluid communication with the catheter shaft guidewire receiving lumen.

An inflatable member, such as a balloon, with proximal and distal ends and an inflatable interior is disposed on the distal section of the catheter shaft. The interior of the balloon is in fluid communication with the inflation lumen. The balloon further includes a distal shaft section adjacent to the balloon distal end with a distally tapered portion. The distal end of the balloon is sealingly secured to the proximal end of the tip member and a portion of the catheter shaft. The distal shaft section tapers distally and forms a tapered distal end with an interior surface defining a portion of the guidewire receiving lumen.

In one embodiment for a method of forming the catheter described above, a catheter assembly is provided which includes a catheter shaft having proximal and distant ends, and a balloon having proximal and distal ends with an inflatable interior and a distal shaft section with an interior surface. A tip member with proximal and distal ends, and a mandrel with proximal and distal ends and a tapered distal portion, are also provided.

The distal end of the catheter shaft is positioned within the interior of the balloon distal shaft section terminating at a point proximal to the balloon distal end. The proximal end of the tip member is positioned adjacent the balloon distal end such that it is distally spaced apart from the catheter shaft distal end. The tapered distal portion of the mandrel is positioned within the interior of the balloon distal shaft section and the tapered distal portion of the mandrel is aligned with the distal end of the balloon distal shaft.

Energy is applied to at least a portion of the balloon distal shaft, bonding such that at least a portion of the balloon distal shaft is bonded to the catheter shaft and at least a portion of the balloon distal shaft section is bonded to the tip member. A distal tip portion of the catheter is formed such that at least a portion of the interior surface of the balloon distal balloon section fluidically connects the catheter shaft and the tip member. Unless stated otherwise, the order in which the steps of the process of making are carried out, are not intended to be limited to the order described.

These and other advantages of the invention will become more apparent from the following detailed description when taken in conjunction with the accompanying exemplary drawings.

BRIEF DESCRIPTION OF THE DRAWINGS

FIG. 4A is a longitudinal cross sectional view, partially in section, of a catheter assembly including a balloon prior to tapering of a balloon distal shaft end and a mandrel having a tapered end.

FIG. 4B is a longitudinal cross sectional, partially cut away, view of the assembly of FIG. 4A with a distal end of the mandrel disposed at the balloon distal end.

FIG. 4C is a longitudinal cross sectional, partially cut away, view of the assembly of FIG. 4B having a shrink tubing disposed on the balloon distal end, and being heated to taper the balloon distal end.

FIG. 4D is a longitudinal cross sectional, partially cut away, view of the assembly of FIG. 4C with the balloon distal end brought together with a proximal end of a tubular member, and being heated to form a bond therebetween.

FIG. 4E is a longitudinal cross sectional, partially cut away, view of the assembly of FIG. 4D with the balloon distal end and the proximal end of the tubular member being heated to form a bond therebetween.

FIG. 4F is a longitudinal cross sectional, partially cut away, view of the assembly of FIG. 4E with the mandrel being pulled out of the catheter.

FIG. 4G is a longitudinal cross sectional, partially cut away, view of the assembly of FIG. 4F including an inner tubular member.

FIG. 4H is a longitudinal cross sectional, partially cut away, view of the assembly of FIG. 4G having a shrink tubing disposed on the balloon distal shaft and being heated to form a bond between the balloon distal shaft and the inner tubular member.

FIG. 4I is a is a longitudinal cross sectional, partially cut away, view of the assembly of FIG. 4H after the formation of the bond between the balloon distal shaft and the inner tubular member.

DETAILED DESCRIPTION OF THE INVENTION

Figure 1:
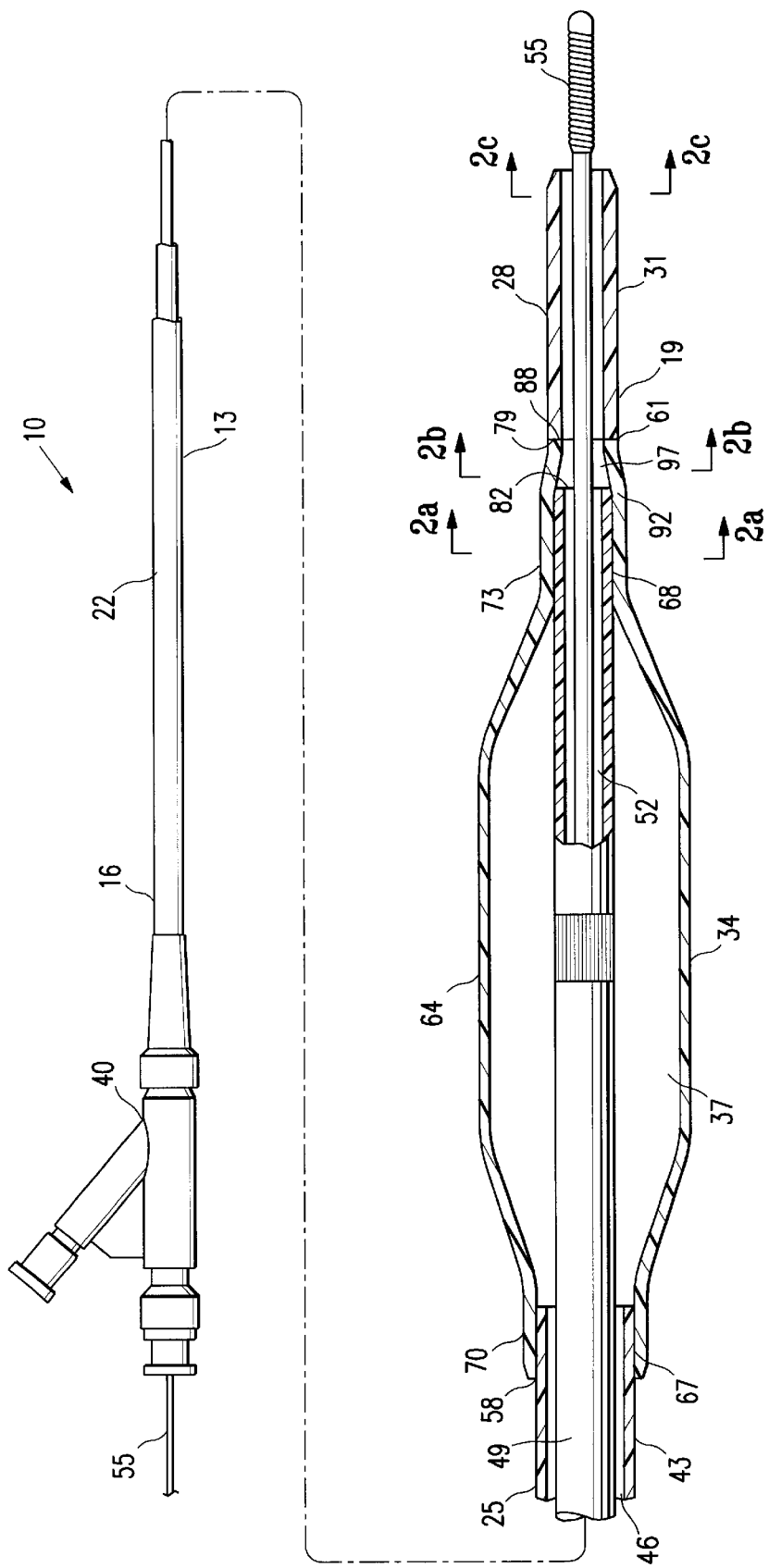
FIG. 1 is an elevational view, partially in section, of a balloon catheter embodying features of the invention, having a tapered distal balloon shaft joined to a distal tip member.
Figure 2C:
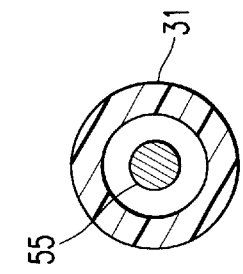
FIG. 2C is a transverse cross-section of the catheter of FIG. 1 taken along lines 2C—2C.
Figure 2B:
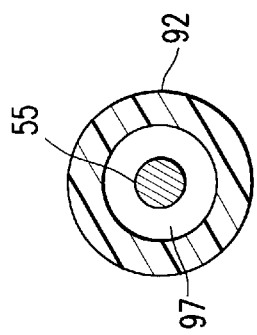
FIG. 2B is a transverse cross-section of the catheter of FIG. 1 taken along lines 2B—2B.
Figure 2A:
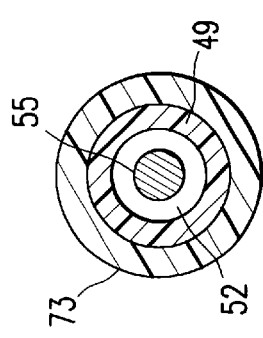
FIG. 2A is a transverse cross-section of the catheter of FIG. 1 taken along lines 2A—2A.

FIGS. 1 and 2A–2C illustrate a balloon catheter 10 embodying features of the invention, comprising an elongated catheter shaft 13 having proximal and distal ends 16 and 19, proximal and distal shaft portions 22 and 25, a distal tip portion 28 including a tip member 31 on the catheter shaft distal end 19, an inflatable balloon 34 on the distal catheter shaft portion 25 having an interior 37, and an adapter 40 on the proximal catheter shaft portion 22 for directing inflation fluid, among other things, to and from the catheter 10.

In the embodiment illustrated in FIG. 1, the catheter shaft distal portion 25 comprises an outer tubular member 43 having an inflation lumen 46, and an inner tubular member 49 having a guidewire receiving lumen 52 disposed within the inflation lumen 46 for slidably receiving a guidewire 55. Balloon 34 has proximal and distal ends 58 and 61 and an intermediate section 64 disposed therebetween. Balloon 34 is sealingly secured to a distal portion 67 of the outer tubular member 43 and a distal portion 68 of the inner tubular member 49 at balloon proximal and distal shaft sections 70 and 73, respectively, the balloon distal shaft section 73 being distally tapered. The balloon interior 37 is in fluid communication with the inflation lumen 46 and the adapter 40.

A proximal end 79 of the tip member 31 is spaced distally apart from a distal end 82 of the inner tubular member 49, and thus is not in contact therewith.

In the embodiment illustrated in FIG. 1, the distal end 82 of the inner tubular member 49 is disposed distally of the inflatable interior 37 of the balloon 34. The balloon distal shaft section 73 is sealingly disposed, in part, about the distal portion 68 of the inner tubular member 49, and forms a joint 88, (e.g. lapjoint, butt-joint) preferably, a butt-joint with the proximal end 79 of the tip member 31. In a presently preferred embodiment, the balloon distal shaft section 73 is secured to both the distal portion 68 of the inner tubular member 49 and the proximal end 79 of the tip member 31, as for example, by fusion bonding.

The distal tip 28 defines in part the guidewire lumen 52. A distal end of the balloon distal shaft 73 is tapered in the distal direction forming a tapered balloon distal end 92. Preferably, inner and outer diameters of the tapered distal end 92 of the distal balloon shaft 73, taper uniformly, that is, at a substantially constant thickness. The distal end 61 of the balloon 34 is longitudinally aligned with the proximal end 79 of the tip member 31. The inner diameter of the guidewire lumen 52 formed by the tapered distal end 92 of the balloon distal shaft 73 is smaller than an inner diameter of the guidewire lumen 52 at a proximal end of the distal shaft section 73, such that the distal end 82 of the inner tubular member 49 terminates proximal to the distal end 61 of the balloon 34, forming a gap 97 between the distal end 82 of the inner tubular member 49 and the proximal end 79 of the tip member 31. The gap 97 has a longitudinal dimension ranging from about 0.25 to about 2 millimeters (mm), preferably, from 0.25 to about 0.5 mm.

In one embodiment, the tip member 31 is tapered in the distal direction. The tip member taper can be continuous or it may include one or more segments of the longitudinal dimension of the tip member. When the entire length of the tip member is not tapered, preferably, the tip member is, at least, tapered at its distal portion.

The distal end of guidewire lumen 52 has an inner diameter configured to allow longitudinal displacement of the guidewire 55 within the guidewire lumen 52, preferably, without frictional engagement of the guidewire 55 centered within the guidewire lumen 52.

The inner diameter of the distal end of the balloon is tapered sufficiently, preferably from about 20° to about 60°, to allow the distal end 82 of the inner tubular member 49 to stop short of the proximal end 79 of the tip member 31; and is preferably, about 3% to about 14%, and more preferably about 7% to about 11% larger than the outer diameter of the guidewire 55 disposable therein. Preferably, the inner diameter of the distal end of the tip member 31 is about 3% to about 14%, preferably about 7% to about 11% larger than the outer diameter of the guidewire 55 disposable therein.

The tip member 31 may be joined to the distal end 61 of the balloon 34 using a variety of suitable means including adhesive bonding, fusing, and hot melt bonding. The tapered distal end 92 of the balloon distal balloon shaft may be formed before, after, or concurrent with the joining of the tip member 31 with the distal end of the distal balloon shaft.

Figure 3:
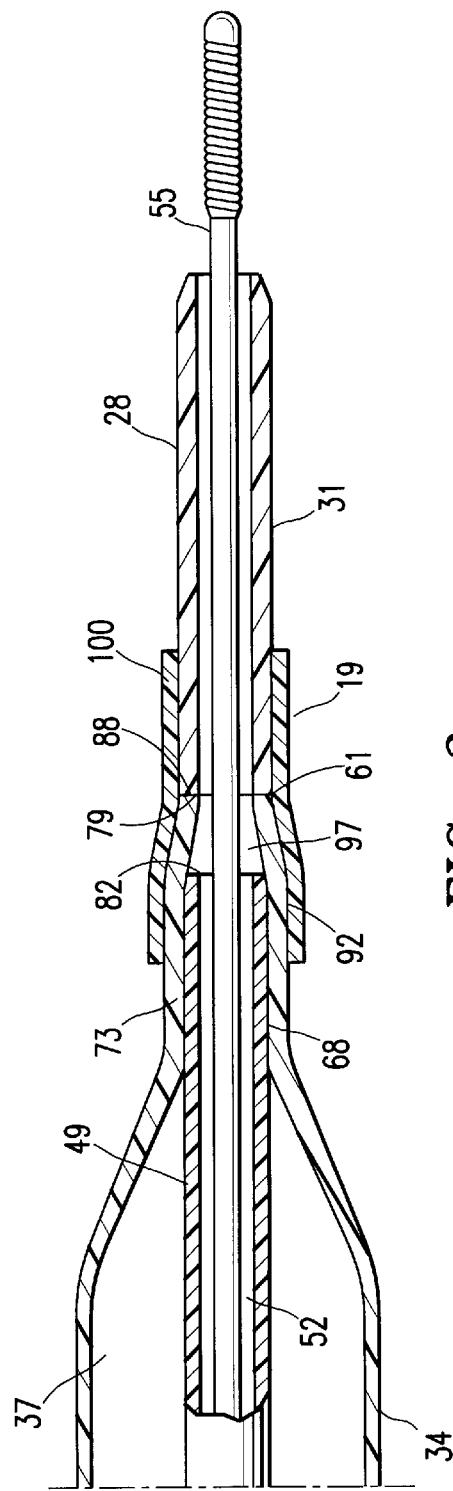
FIG. 3 is a longitudinal cross sectional, partially cutaway, view of the catheter of FIG. 1 showing a sheath disposed about at least a portion of the distal portion of the balloon distal shaft and the proximal portion of the tip member including the joint area.

As shown in FIG. 3, a sheath 100 can be disposed about at least a portion of the distal portion of the balloon distal shaft and the proximal portion of the tip member including the joint area 88.

FIGS. 4A through 4I illustrate one embodiment of a method of making distal tip portion 28 (similar to that in FIG. 1) using a mandrel 200 having a tapered distal portion 203 corresponding to the balloon tapered distal end 92 of the balloon distal shaft 73. The method generally comprises providing a catheter assembly 206 including a balloon 34' on a distal shaft portion 25'. A distal end 209 of the mandrel 200 is inserted into the catheter assembly 206 at a point proximal to the balloon 34'. In the embodiment shown, the mandrel is inserted at the proximal end of the catheter assembly 206. However, it should be appreciated that in making a rapid exchange type catheter, the mandrel could be introduced into the catheter assembly at a point much proximally closer to the balloon.

The mandrel distal end 209 is advanced distally through the balloon distal shaft terminating at the balloon distal end, preferably extending distally beyond the balloon distal end.

Preferably, a shrink tubing 213 is placed on at least a distal portion of the outer surface of balloon distal shaft and the area is heated, as by exposure to a laser, to apply heat and radially compressive pressure conforming the distal end of the balloon distal shaft to the mandrel tapered surface 219, forming a tapered balloon distal shaft 92'. The shrink tubing 213 is thereafter removed.

A tubular member 31' for forming the tip member 31, and the balloon distal shaft are brought together, preferably in abutting relationship. Preferably, a shrink tubing 216 is placed on at least a proximal portion of the outer surface of tubular member 31' and at least a distal portion of the tapered balloon distal shaft 92', and the area is heated, as by exposure to a laser, to apply heat and radially compressive pressure, and a joint, preferably a butt-joint 88' is formed between the two ends, 79' and 61'. The tapered mandrel 200 is then removed, by being pulled in the proximal direction.

A distal end of an inner member 49' is advanced through a balloon interior until it butts against an inner surface of the balloon distal shaft tapered area.

A distal end of a mandrel 225 is inserted into the catheter assembly 206 at a point proximal to the balloon 34' and is advanced distally beyond the balloon proximal shaft, preferably within the balloon interior. In the embodiment shown, the mandrel is inserted at the proximal end of the catheter assembly. However, it should be appreciated that in making catheters of different type, such as rapid exchange, the mandrel can be introduced at a point much proximally closer to the balloon.

Preferably, a shrink tubing 226 is placed on at least a proximal portion of the outer surface of the balloon distal shaft 73', and the area is heated, as by exposure to a laser, to apply heat and radially compressive pressure to the proximal portion of the balloon distal shaft 73' conforming the proximal portion of the balloon distal shaft to the distal end of the inner tubular member surface 228, forming a distal balloon seal 231 between at least a portion of the inner surface of the balloon distal shaft and at least a portion of the outer surface of the inner tubular member 49'. The shrink tubing 226 is thereafter removed and a catheter having features similar to that of FIG. 1 is formed.

Figure 5:
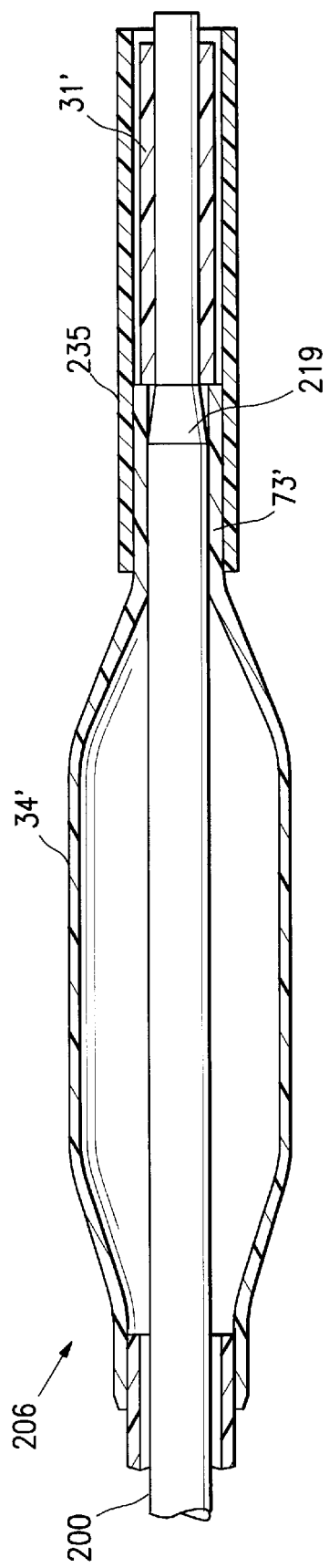
FIG. 5 is a longitudinal cross sectional view, partially in section, of a catheter assembly and mandrel as used in an alternate method of making.

Alternatively, as shown in FIG. 5, the forming of the joint between the tubular member 31' and the balloon distal shaft 73' can happen concurrent with the tapering of the balloon distal shaft. In this embodiment the tapered mandrel 200 is placed in the appropriate position as described above. The distal end of the balloon distal shaft and the proximal end of the tubular member 31' are brought together, as described above. Preferably, a shrink tubing 235 is placed over at least the distal portion of the distal balloon shaft, and extending distally beyond the joint area between the distal end of the balloon distal shaft and the proximal end of the tubular member 31'. The desired area is then heated to form the appropriate tapers and bonds as described above.

Alternative, or in combination with the heating process, other suitable means, such as adhesives, can be used to form any or all of the necessary seals and joints.

The dimensions of catheter 10 are determined largely by the size of the guidewires to be employed and the size of the artery or other body lumen through which the catheter must pass or the size of the stent being delivered. Typically, the outer tubular member 46 has an outer diameter of about 0.02 to about 0.04 inches (in.) (0.05 to 0.10 cm), usually about 0.037 in. (0.094 cm), an inner diameter of about 0.015 to about 0.035 in. (0.038 to 0.089 cm), usually about 0.03 in. (0.076 cm). The wall thickness of the outer tubular member 46 can vary from about 0.002 to about 0.008 in. (0.0051 to 0.0201 cm), typically about 0.003 in. (0.0076 cm). The inner tubular member 49 typically has an outer diameter of about 0.019 to about 0.028 in., usually about 0.021 in. The overall working length of the catheter 10 may range from about 100 to about 150 cm, and is typically about 147 cm. Preferably, balloon 34 may have a length from about 0.5 cm to about 8 cm, more preferably from about 0.5 cm to about 4 cm, and typically about 2 cm with an inflated working diameter of about 1 to about 8 mm, and for coronary applications about 1.5 mm to about 5 mm. The balloon has a thickness ranging from about 0.0005 to about 0.001 in., more preferably, from about 0.0005 to about 0.00075 in.

The various catheter components can be formed of suitable materials. The tubular members (e.g., inner tubular member, outer tubular member, tip member) are formed of material, or include material thereon, compatible with the balloon material to allow formation of appropriate joints therebetween.

In a presently preferred embodiment, the tip member 31 is formed of a polymeric material similar to or different from the material forming the balloon 34. The tip member 31 may be a soft tip configured to provide an atraumatic distal end on the catheter to minimize injury to the patient's vasculature during advancement of the catheter therein. In one embodiment, the tip member 31 is formed of a polymeric material similar to that forming the balloon 34 but having a lower Shore Durometer hardness than the polymeric material forming a section of the balloon proximal thereto. For example, the balloon material may be selected from material with hardness 60 and above, more preferably from about 63 to about 72; with the tip member 31 formed of a material having a hardness of 65 and below, more preferably from about 63 to about 55, on a Shore D scale.

A variety of polymeric materials may be used to form the tip member 31 including polyamides such as PEBAX (polyether block amide) and polyethylene based adhesives such as PRIMACOR, high density polyethylene (HDPE), polyurethane, and polyesters such as HYTREL. However, the choice of material depends on a variety of factors including the desired application and the method used to make the tip member 31.

To the extent not discussed herein, the various catheter components can be formed of conventional materials. Outer tubular member 46 and the inner tubular member 49 can be formed by conventional techniques, for example by extruding, from materials already found useful in intravascular catheters such a polyethylene, polyvinyl chloride, polyesters, polyamides, polyimides and composite materials. The various components may be joined by heat bonding or use of adhesives. The various components such as the inner balloon, member, and soft tip should be selected of compatible material of the proper joining of the same.

A variety of suitable catheter designs may be used, including rapid exchange, over-the-wire, and fixed wire catheter designs. A rapid exchange catheter generally includes an inflation lumen extending from the proximal end of the catheter shaft to a location spaced proximal to the distal end of the catheter shaft, a distal guidewire port in the distal end of the catheter shaft, a proximal guidewire port spaced distal to the proximal end of the catheter shaft, and a guidewire lumen extending between the proximal and distal guidewire ports. Typically, the proximal guidewire port is spaced a substantial distance from the proximal end of the catheter shaft and a relatively short distance from the distal guidewire port, so that the proximal guidewire port is closer to the distal guidewire port than to the proximal end of the catheter shaft.

Although not illustrated, the balloon catheter of the invention may be used to deliver prostheses, such as expandable stents, grafts, and the like, to a desired location within the patient's vasculature. A stent (not shown) comprising an expandable tubular body, typically having an open-walled structure, may be mounted on balloon 34, and balloon 34 may be inflated to expand the stent and seat it in the vessel. Additionally, catheter 10 may be used to touch up a previously implanted stent by positioning balloon within stent lumen and expanding the balloon to further expand the stent within a body lumen.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A balloon catheter, comprising:
   an elongated catheter shaft having a proximal end, a distal end, a proximal shaft section, a distal shaft section, a guidewire lumen extending along at least a portion thereof to a port at the catheter shaft distal end, and an inflation lumen;
   a distal tip member having a proximal end spaced distally apart from the distal end of the elongated catheter shaft, and being in fluid communication with the catheter shaft guidewire lumen, and defining a guidewire distal port; and
   a balloon on the distal catheter shaft section, having an inflatable interior in fluid communication with the inflation lumen, a proximal balloon shaft section, and a distal balloon shaft section tapering distally with a distal end butt-joined to the proximal end of the tip member and with an interior surface defining a portion of the guidewire lumen, the distal balloon shaft being sealingly secured to the catheter shaft and the tip member.

2. The catheter of claim 1 wherein the balloon inflatable interior is spaced proximal to the distal end of the catheter shaft.

3. The catheter of claim 1 wherein the distal balloon shaft has a uniform thickness.

4. The catheter of claim 1 wherein the distal balloon shaft has proximal and distal ends, and a portion located between the proximal and distal ends of the distal balloon shaft, said distal balloon shaft portion tapering distally from a location proximal to the distal end of the elongated catheter shaft to a location distal to the distal end of the elongated catheter shaft, so that an inner diameter of the distal end of the distal balloon shaft is smaller than an inner diameter of the proximal end of the distal balloon shaft and is the same as an inner diameter of at least a section of the distal tip member.

5. The catheter of claim 1 wherein the distal tip member and the distal balloon shaft both have at least a section thereof having an inner diameter which is the same as an inner diameter of a distal-most end portion of the elongated catheter shaft.

6. The catheter of claim 1, wherein the proximal end of the tip member is spaced apart from the distal end of the catheter shaft by about 0.25 to about 2 millimeters.

7. The catheter of claim 1, wherein the proximal end of the tip member is spaced apart from the distal end of the catheter shaft by about 0.25 to about 1.5 millimeters.

8. The balloon catheter of claim 1 wherein the catheter shaft comprises an outer tubular member defining the inflation lumen and an inner tubular member disposed within at least a portion of the outer tubular member and defining at least in part the guidewire receiving lumen, the inner tubular member having a distal end extending through the balloon interior and being proximally spaced apart from the proximal end of the tip member.

* * * * *

UNITED STATES PATENT AND TRADEMARK OFFICE
CERTIFICATE OF CORRECTION

PATENT NO. : 6,692,461 B2 Page 1 of 1
DATED : February 17, 2004
INVENTOR(S) : Kenneth L. Wantink It is certified that error appears in the above-identified patent and that said Letters Patent is hereby corrected as shown below:

Column 3,
Line 1, insert -- FIG. 2 is a transverse cross sectional view of FIG. 1 taken along line 2-2 --.

Signed and Sealed this

Fourteenth Day of September, 2004

JON W. DUDAS
*Director of the United States Patent and Trademark Office*